United States Patent [19]

Voskuil et al.

[11] 3,941,845

[45] Mar. 2, 1976

[54] PROCESS FOR PREPARING CYCLOALKANONES AND CYCLOALKANOLS

[75] Inventors: Willem Voskuil, Sittard; Joseph J. M. van der Donck, Geleen, both of Netherlands

[73] Assignee: Stamicarbon, B.V., Geleen, Netherlands

[22] Filed: Oct. 19, 1973

[21] Appl. No.: 408,049

[30] Foreign Application Priority Data

Oct. 21, 1972 Netherlands ................... 7214299

[52] U.S. Cl. ...... 260/586 R; 260/610 B; 260/631 R
[51] Int. Cl.$^2$ C07C 27/04; C07C 29/00; C07C 45/00
[58] Field of Search ......... 260/586 R, 586 B, 610 B, 260/631 R, 621 C

[56] References Cited
UNITED STATES PATENTS

| | | | |
|---|---|---|---|
| 2,218,457 | 10/1940 | Winans | 260/586 R |
| 2,462,103 | 2/1949 | Johnson | 260/610 B |
| 2,497,349 | 2/1950 | Farkas | 260/610 B |
| 2,671,809 | 3/1954 | Forturn et al. | 260/621 C |
| 2,851,496 | 9/1958 | Cates et al. | 260/631 R |
| 3,187,052 | 6/1965 | Nelson et al. | 260/621 C |
| 3,422,146 | 1/1969 | Defoor | 260/586 R |

OTHER PUBLICATIONS

"Kogyo Kagaku Zasshi," Vol. 73, pp. 2056–2058, (1970).

*Primary Examiner*—Norman Morgenstern
*Attorney, Agent, or Firm*—Cushman, Darby & Cushman

[57] ABSTRACT

Cycloalkanones and cycloalkanols can be prepared by conversion of cycloalkylhydroperoxides in solution in a suitable solvent, under the influence of a solid catalyst, Solution and catalyst form a heterogeneous system. For this purpose, a number of catalysts have been proposed, but the known processes have serious drawbacks with respect to efficiency of the process, catalyst cost and/or alcohol to ketone ratio obtained.

According to the invention, cycloalkanones and cycloalkanols are prepared by conversion of cycloalkylhydroperoxides having 5–12 carbon atoms in the ring under the influence of a heterogeneous catalyst comprising copper oxide, at a temperature below 160°C. Preferably, copper - chromium - oxide is applied as a catalyst.

7 Claims, No Drawings

PROCESS FOR PREPARING CYCLOALKANONES AND CYCLOALKANOLS

The invention relates to a process for preparing cycloalkanones and cycloalkanols by conversion of cycloalkylhydroperoxides under the influence of a heterogeneous catalyst.

A process of this type is disclosed in Kogyo Kagaku Zasshi 73 (1970), 2056-8. From this article it appears that cyclohexylhydroperoxide can be converted in cyclohexane solution under the influence of some metaloxides and -sulfides. Amongst the oxides and sulfides examined, some were active as a catalyst for the conversion of cyclohexylhydroperoxide into cyclohexanol and cyclohexanone and others were not.

In the preparation of cycloalkanones and cycloalkanols from cycloalkylhydroperoxides it is of importance to work at a temperature at which the non-catalyzed, thermal decomposition of the cycloalkylhydroperoxide reaction competes as little as possible with the total conversion of the cycloalkylhydroperoxide and the catalyzed conversion as large as possible a contribution. For, in comparison with the catalyzed conversion, the thermal decomposition of the peroxide shows little specificity to the production of the desired products, cycloalkanone and cycloalkanol. In the thermal decomposition a relatively large amount of undesirable by-product is formed. At temperatures of over about 120° C the thermal decomposition of the peroxide proceeds at a clearly perceptible rate. It is desirable therefore to work at a temperature of below approximately 120° C, preferably of below 100° C. Below 80° C the speed of the thermal decomposition reaction is so small as to be negligible.

The aforementioned article does not indicate any catalysts with the aid of which aforementioned objectives could be reasonably achieved. It is mentioned that at 70° C cobalt(III)oxide is not active at all, and that molybdenum sulfide is only active if present in a large quantity and even then is active to only a low degree. Temperatures of 120° C and higher are necessary to cause the conversion desired to proceed at a satisfactory rate. These high temperatures lead to a decrease in efficiency.

In the U.S. Pat. Spec. No. 2,851,496 a process is disclosed for the preparation of cyclohexanone and cyclohexanol, in which in a first step cyclohexane in the liquid phase is oxidized with air in the presence of a homogeneous catalyst, like cobalt-naphthenate and, in a second step, the reaction mixture of the first step is passed over a heterogeneous catalyst, for instance cobalt(II)oxide, vanadium oxide-on-aluminium oxide, molybdenum sulfide or cobalt oxide-on-charcoal, at a temperature of, for instance, 70° C. The reaction mixture of the first step contains cyclohexylhydroperoxide, which is converted for the larger part into cyclohexanone and cyclohexanol in the second step. The quantity of heterogeneous catalyst used is not indicated.

From experiments conducted by Applicant however it has appeared that a very large amount of catalyst is needed in order to achieve a satisfactory conversion rate with the catalysts known from said U.S. patent specification, and, hence, the catalyst costs of this known process are high. This holds, a fortiori, if the catalysts containing noble metal are used as mentioned in said patent specification.

It has now been found that with application of oxidic copper catalysts high conversion rates of cycloalkylhydroperoxides into cycloalkanones and cycloalkanols can be achieved already at low temperatures, for instance temperatures of between 50° and 100° C. This is highly surprising, seeing that in the quoted article from Kogyo Kagaku Zasshi it is mentioned that the half-value time of cyclohexylhydroperoxide in cyclohexane as a solvent at 160° C in the presence of copper(II)oxide amounts to 58 minutes, which is only little shorter than the other half-value time mentioned in this article, viz. that of cyclohexylhydroperoxide, under the same conditions, but in the absence of a catalyst, i.e. 65 minutes.

According to the invention cycloalkanones and cycloalkanols are prepared by converting cycloalkylhydroperoxides with 5-12 carbon atoms in the ring at a temperature of below 160° C under the influence of an oxidic copper catalyst.

With the application of the catalysts according to the invention extremely high specific conversion rates (s.c.r.), expressed in moles of cycloalkylhydroperoxide converted per kg of heterogeneous catalyst per hour at 80° C, can be achieved. With the aid of copper(II)oxide prepared by heating basic copper(II)carbonate at 300° C in an air stream, for instance, a s.c.r. of 75 or even considerably higher can be reached. This number can be compared with the number of molybdenum sulfide at 70° C, viz. 10, calculated on the basis of the data contained in the quoted article from Kogyo Kagaku Zasshi.

The selectivity of the conversion according to the invention to the desired products cycloalkanone and cycloalkanol is high and amounts to 95-100%, based on the converted peroxide. This means that 0-5% of the peroxide is converted into by-products. If working in cycloalkane as a solvent, which cycloalkane corresponds to the cycloalkylhydroperoxide, one sometimes finds an apparent efficiency of more than 100%. This phenomenon is well-known in this kind of reactions and is brought about by oxidation of some solvent with the peroxide. Also in this case at most 5% of the peroxide plus the converted cycloalkane are converted into by-products.

A matter of importance in the preparation of cycloalkanones and cycloalkanols from cycloalkylhydroperoxides is the ratio in which the ketone and the alcohol are obtained. For most applications preferably more alkanone is produced than cycloalkanol. From experiments carried out by applicant it appeared that the alcohol to ketone ratio in the reaction product of the decomposition of cyclohexylhydroperoxide at 80° C in cyclohexane as a solvent with one of the known catalysts cobalt(II)oxide, vanadium oxide or platinum lies between 1.1 and 2.4. If copper(II)oxide, which is not supported on a carrier, is applied as a catalyst, said ratio lies between 2.1 and 2.8, dependent on the way in which the copper(II)oxide has been prepared.

The copper-chromium-oxide catalyst system has particularly favourable properties. This catalyst system is an active one, with which cycloalkanone and cycloalkanol efficiencies of 98% or higher can be achieved at alcohol to ketone ratios of 0.3 or less.

The catalysts according to the process of the invention may or may not be supported on a carrier. Suitable carrier materials are silica, alumina, carbon and the like.

The process according to the invention is by preference carried out at a temperature of between 30° and 120° C. At temperatures lower than 30° C the conversion rate is insufficiently large. For reasons already mentioned above, usually a lower efficiency in the desired products is obtained at temperatures above 120° C, unless an exceptionally active catalyst system is applied. The 60°–100° C temperature range constitutes a proper compromise between a small reaction speed at a low temperature and a small selectivity at a high temperature.

The reaction pressure is not critical. Generally, the reaction is carried out with a solution of the cycloalkylhydroperoxide in a liquid distributing agent, so that it will then become necessary to apply a pressure at which a liquid phase is maintained in the system. For technical reasons, a pressure of 1 atmosphere or slightly higher is preferred, although also lower and higher pressures, for instance of 0.1–20 atmospheres, may be applied, dependent on the distributing agent and the cycloalkylhydroperoxide used.

As a distributing agent, distributing agents are to be considered that are inert under the reaction conditions, as well as the cycloalkane which corresponds to the cycloalkylhydroperoxide used. Said cycloalkane is given preference because in this case more than one molecule of cycloalkanone or cycloalkanol can form to every molecule of cycloalkydroperoxide used. Examples of suitable inert distributing agents are aromatic hydrocarbons, like benzene.

The cycloalkylhydroperoxide may be prepared by oxidation of the corresponding cycloalkane in the liquid phase at elevated temperature with an oxygen-containing gas, such as air. Low conversions on the basis of cycloalkane supplied, for instance 1–12%, are worked at. Suitable oxidation temperatures lie between 120° and 200° C; preferably, the work is carried out at a temperature of between 140° and 180° C. The operating pressure is not critical but should be such that a liquid phase is maintained in the system. Usually, the pressure lies between 4 and 50 atmospheres.

By preference the oxidation reaction is carried out in the absence of substances which promote the decomposition of cycloalkylhydroperoxide, like compounds of transition metals, which compounds act as oxidation catalysts. In order to achieve this object reactors having an inert internal wall, for instance of passivated steel, aluminium, tantalum, glass, enamel and the like, may be applied. In this way the aspecific decomposition of the cycloalkylhydroperoxide at the oxidation temperature which is generally relatively high is avoided as much as possible.

The oxidation reaction yields a hot, rather dilute solution of cycloalkylhydroperoxide in cycloalkane, which solution is under pressure. It is appropriate for this solution or suspension to be subsequently expanded to a lower pressure, for instance to approximately 1 atmosphere. If the cycloalkane should be cyclopentane, cyclohexane or cycloheptane, such an amount of cycloalkane will evaporate during said expansion that the temperature drops to 60°–100° C, which is a highly suitable temperature range for the conversion according to the invention, so that the concentrated solution obtained, which contains cycloalkylhydroperoxide, can be subjected to the process according to the invention without further measures. However, it would serve a good purpose for the crude solution to be stripped, at least partly, from any contaminants, for instance by washing it with water. In this way fouling of the catalyst is opposed. It is also possible first to separate off pure cycloalkylhydroperoxide from the oxidation product mixture, for instance by extraction with an aqueous alkaline solution, followed by acidulation and further processing of the extract, and to use the pure peroxide as a starting material.

The invention will now be elucidated by means of the following examples.

EXAMPLE I

Basic copper(II)carbonate of the composition $Cu_2(OH)_2CO_3$ was heated for 3 hours at 300° C, whilst air was passed over, during which it changed over into copper(II)oxide.

500 mg of the copper(II)oxide prepared in this way were added to 60 ml of a 0.21 molar solution of cyclohexylhydroperoxide in cyclohexane. The whole was stirred for 15 minutes at a temperature of 80° C. Upon completion, all of the cyclohexylhydroperoxide appeared to have been converted. The cyclohexanol and cyclohexanone efficiency amounted to 106% at an alcohol to ketone ratio of 2.9.

EXAMPLE II

The procedure of example I was repeated, however with use of 26 mg of catalyst and 34 ml of a 0.09 molar peroxide solution. After 60 minutes 59% of the cyclohexylhydroperoxide had been converted at an efficiency in cyclohexanone and cyclohexanol of 104% and an alcohol to ketone ratio of 2.9.

EXAMPLE III

The procedure of example I was repeated, however with use of benzene instead of cyclohexane as a solvent. The degree of conversion amounted to 93%, the efficiency to 95% and the alcohol to ketone ratio to 2.8.

EXAMPLE IV

Commercially available copper(II)oxide was heated for 2 hours at 300° C, whilst air was passed over. 500 mg of the copper(II)oxide so treated were added to 60 ml of a 0.21 molar solution of cyclohexylhydroperoxide in cyclohexane. After 60 minutes' stirring at 80° C 77% of the peroxide had been converted at an efficiency in cyclohexanone and cyclohexanol of 105% at a ratio between alcohol and ketone of 2.1.

EXAMPLE V

In a reaction vessel having a volume of 5 litres and being provided with a stirrer, a reflux cooler, a thermometer, a pH-measuring electrode system and a feed vessel, 50 grams of Aerosil 130 V were suspended in 2 litres of demineralized water. The temperature was raised to 80° C and the pH value of the solution was set to 8.5 – 8.6 by addition of soda lye. Whilst the pH was kept at this value, a solution A and a solution B were simultaneously added by means of the feed vessel, with continuous stirring.

Solution A was a solution of 61.1 grams (0.154 mole) of $Cr(NO_3)_3 \cdot 9 H_2O$ and 160 grams (0.664 mole) of $CuSO_4 \cdot 6 H_2O$ in 600 ml of demineralized water, acidulated with 12 ml of 65% by weight nitric acid. Total volume about 775 ml.

Solution B was a solution of 80 grams (2 moles) of NaOH in 700 ml of demineralized water.

The pH value was kept constant by bringing the feed rates for A and B into accord by means of two pumps. The feed rate amounted to 350–400 ml/h. After the solutions were completely added the two feed pumps were flushed with 100 ml of demineralized water, whilst the temperature of the reactor vessel contents was raised to 100° C. After cooling to 60°–70° C. the deposit was filtered off, washed with 1500 ml of demineralized water whose pH had been brought to about 8 with the aid of a sodium hydroxide solution, and subsequently dried for 18 hours at 120° C in a drying oven.

The weight of the dark-green mass amounted to 229 grams, the mass containing Cu to 23.4%, Cr to 4.2%, $SiO_2$ to 42.1% and Na to 2.7%.

2000 mg of this catalyst were added to 60 ml of a 0.22 molar solution of cyclohexylhydroperoxide in cyclohexane and the whole was stirred at a temperature of 80° C. After 1 hour, the degree of conversion amounted to 100%, the efficiency to 87% and the alcohol to ketone ratio to 0.2. The catalyst was filtered off, washed with cyclohexane and added to a new batch of peroxide solution. After 1 hour's stirring at 80° C the degree of conversion now amounted to 99%, the efficiency in cyclohexanone and cyclohexanol to 99% and the alcohol to ketone ratio to 0.3.

EXAMPLE VI 260 mg of catalyst prepared in the way of example V were added to 40 ml of a 0.11 molar solution of cyclohexylhydroperoxide in cyclohexane, and the whole was stirred for 1 hour at a temperature of 80° C. The peroxide was converted to 99%, with an efficiency in the desired products of 99% at an alcohol to ketone ratio of 0.3.

EXAMPLE VII

When, according to the procedure of example VI, 32 ml of a 0.10 molar peroxide solution were converted under the influence of 60 mg of catalyst, the degree of conversion was 86%, the efficiency 104% and the alcohol to ketone ratio 0.3.

EXAMPLE VIII

Through oxidation of cyclohexane in the liquid phase, with air as an oxidizing agent, an oxidation mixture was prepared which, by the side of cyclohexane, contained 317 mmoles/kg of cyclohexylhydroperoxide, 222 mmoles/kg of cyclohexanol and 155 mmoles/kg of cyclohexanone. The mixture further contained 71 mgeq/kg of organic acids.

1.10 grams of copper-chromium-oxide catalyst, prepared as in example V, were added to 48 grams of oxidation mixture. After 1 hour's reaction at 80° C, 97% of the peroxide had decomposed. The efficiency in cyclohexanol and cyclohexanone amounted to 99% at an alcohol to ketone ratio of 0.6.

EXAMPLE IX

Through oxidation of cyclohexane in the liquid phase, with air as an oxidizing agent, followed by the reaction mixture being washed with water, an oxidation mixture was prepared which, by the side of cyclohexane, contained 280 mmoles/kg of cyclohexylhydroperoxide, 199 mmoles/kg of cyclohexanol, 186 mmoles/kg of cyclohexanone and 34 mgeq/kg of organic acids.

1.29 grams of copper-chromium-oxide catalyst, prepared as in Example V, were added to 65 grams of oxidation mixture and the whole was kept to a temperature of 80° C whilst being stirred. After 1 hour 98% of the peroxide had been converted. The efficiency amounted to 106% and the alcohol to ketone ratio to 0.7, calculated after cyclohexanol and cyclohexanone already present in the oxidation mixture had been subtracted.

The catalyst was filtered off, washed with cyclohexane and added to a new batch of oxidation mixture. After 1 hour's stirring at 80° C 96% of the peroxide present in the new batch had been converted into cyclohexanone and cyclohexanol to an efficiency of 112%. The alcohol to ketone was 0.7.

The catalyst was filtered off once again, washed with cyclohexane and added to a third batch of oxidation mixture. After 1 hour's stirring at 80° C again 96% of the peroxide had been converted. The efficiency amounted to 117% and the ratio between alcohol and ketone to 0.7.

We claim:

1. In a process for the preparation of a corresponding cycloalkanone and cycloalkanol by heterogeneous catalytic liquid phase conversion of a cycloalkylhydroperoxide, having 5 to 12 carbon atoms in the ring, the improvement which comprises using a heterogeneous catalyst comprising copper (II)-chromiumoxide in a cycloalkane or aromatic hydrocarbon distributing agent at a temperature of at least 30° C. and below 160° C.

2. Process according to claim 1 wherein said the copper-chromium-oxide is prepared by co-precipitation of copper hydroxide and chromium hydroxide.

3. Process according to claim 1, wherein the reaction is carried out at a temperature below 120° C.

4. Process according to claim 3, characterized in that the reaction is carried out at a temperature between 60° and 100° C.

5. Process according to claim 1, wherein a solution of a cycloalkylhydroperoxide in the corresponding cycloalkane, is prepared by oxidation of the cycloalkane in the liquid phase with a molecular oxygen containing gas oxidizing agent.

6. Process according to claim 5, characterized in that the reaction mixture of an oxidation reaction of cycloalkane, which mixture is to be used as a starting material, is washed with water.

7. The process of claim 1 wherein said cycloalkylhydroperoxide is prepared by the liquid phase oxidation of a cycloalkane having 5 to 12 carbon atoms in the ring with a molecular oxygen containing gas oxidizing agent.

* * * * *